United States Patent [19]
Wasserman

[11] Patent Number: 5,205,812
[45] Date of Patent: Apr. 27, 1993

[54] HAND SPLINT

[75] Inventor: Constance V. Wasserman, Mill Valley, Calif.

[73] Assignee: L'Nard Associates, Inc., St. Petersburg, Fla.

[21] Appl. No.: 819,988

[22] Filed: Jan. 13, 1992

[51] Int. Cl.$^5$ .......................... A61F 5/00; A61F 5/37
[52] U.S. Cl. ........................................ 602/5; 602/20; 602/21; 128/878
[58] Field of Search .................. 602/20, 21, 5; 128/77, 128/87 R, 87 A, 88, 89 R, 878, 879, DIG. 15, 846

[56] References Cited

U.S. PATENT DOCUMENTS

| | | | |
|---|---|---|---|
| 1,328,598 | 1/1920 | Schilling | 602/21 |
| 2,318,864 | 5/1943 | Jackson | 602/21 |
| 3,776,225 | 12/1973 | Lonardo | 128/DIG. 15 |
| 4,558,694 | 12/1985 | Barber | 602/21 |
| 4,662,364 | 5/1987 | Viegus | 602/21 |
| 4,782,825 | 11/1988 | Lonardo | 602/21 |
| 4,960,114 | 10/1990 | Dale | 602/21 |
| 4,977,890 | 12/1990 | Mann | 602/21 |
| 5,020,515 | 6/1991 | Munn | 602/21 |
| 5,056,504 | 10/1991 | Mann | 602/21 |

Primary Examiner—Robert A. Hafer
Assistant Examiner—Michael Brown
Attorney, Agent, or Firm—Zarley, McKee, Thomte, Voorhees & Sease

[57] ABSTRACT

A contour hand splint having an elongated base member for attachment to the forearm and wrist of a patient, with a lower end terminating adjacent the patient's fingers. A crossbar extends across the lower end of the base member. A resilient pad extends along the inner surface of the base member, and a flexible resilient pad member is wrapped around the crossbar to receive and support the curved fingers of a patient suffering from finger contractures. Strap means secured to the base member with fasteners thereon secure the splint to the patient's arm and wrist.

4 Claims, 2 Drawing Sheets

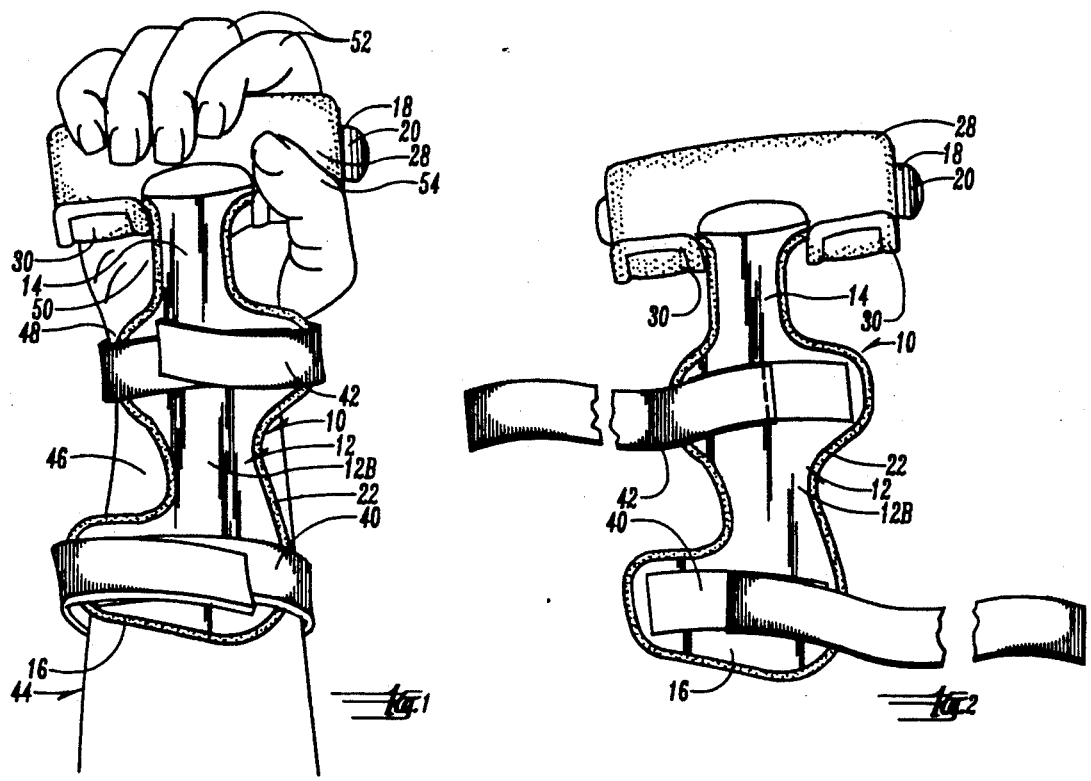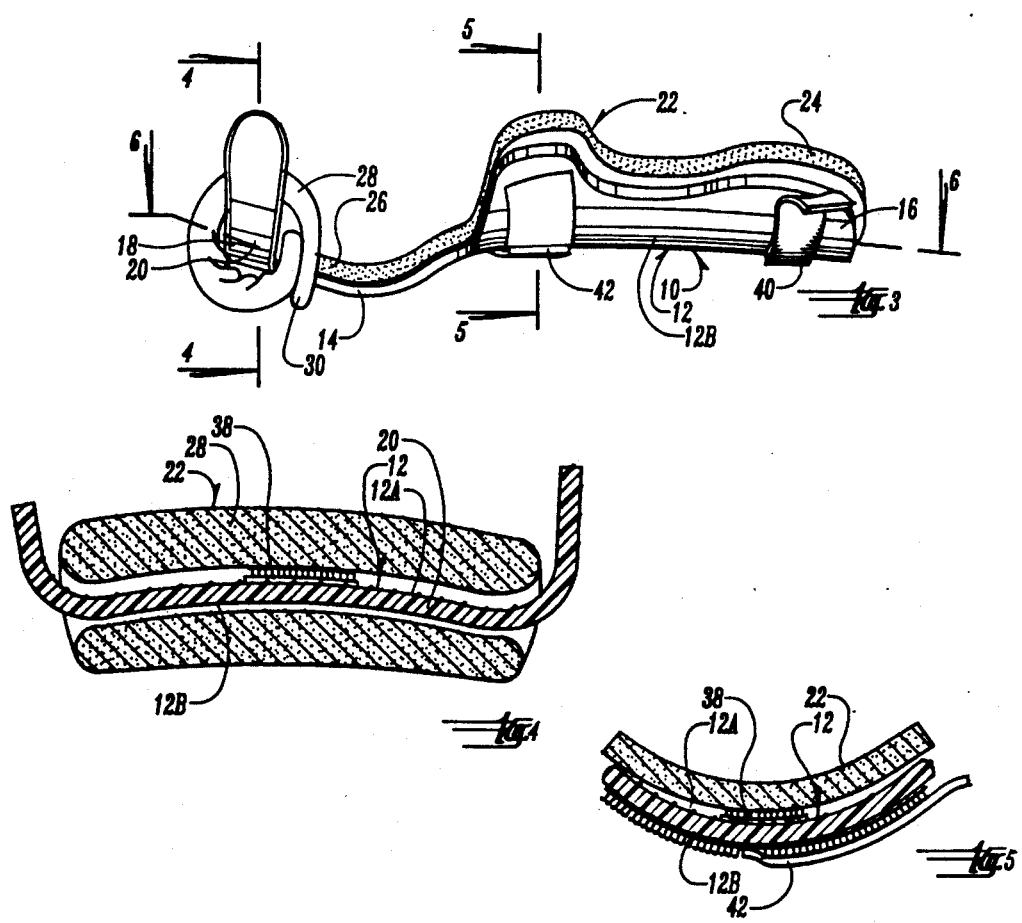

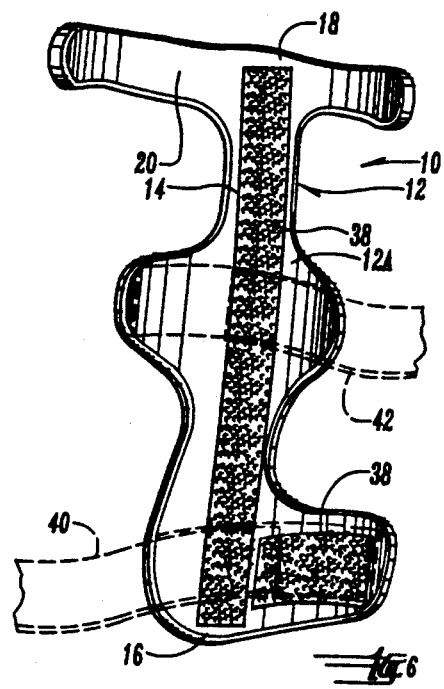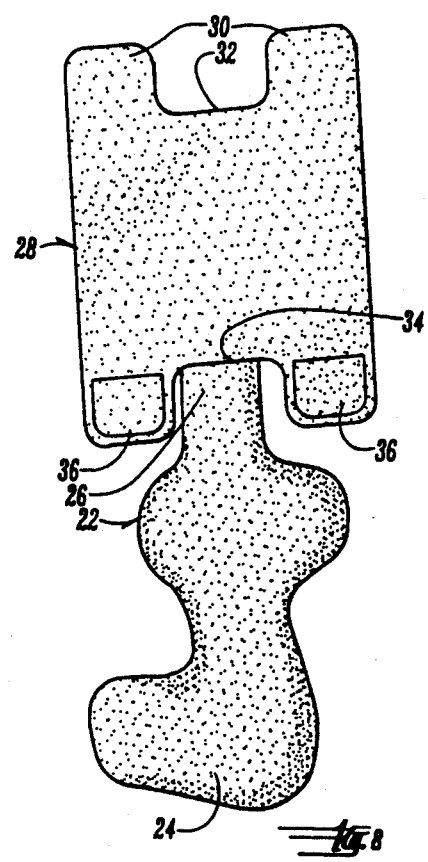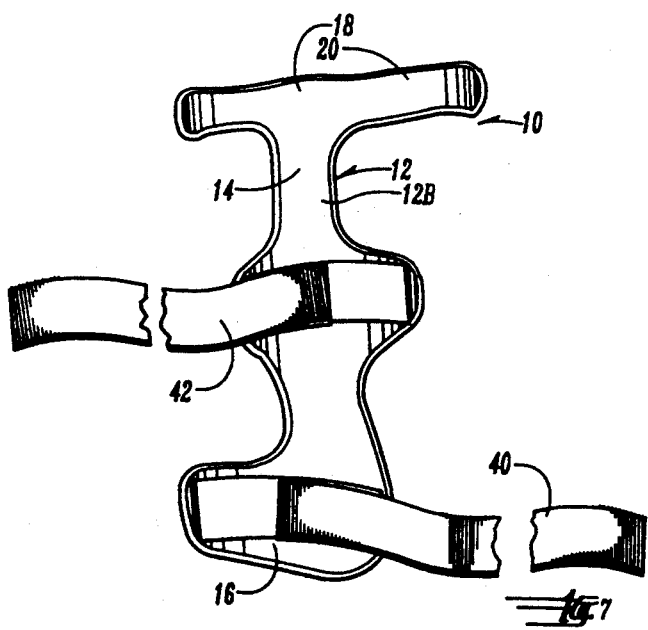

HAND SPLINT

BACKGROUND OF THE INVENTION

Hand splints are common in the prior art to deal with a plurality of wrist, hand and finger problems. However, the splints typically do not provide relief for patients who are in the advanced stages of finger contractures. See, for example, U.S. Pat. No. 3,776,225.

It is therefore a principal object of this invention to provide a hand splint for patients who are in the advanced stages of finger contracture.

A further object of this invention is to provide a hand splint which can accommodate patients who are experiencing finger contractures and which can provide comfort to the patient's fingers.

A still further object of this invention is to provide a hand splint for patients suffering from finger contracture which can create a comfortable pad element for the fingers adaptable for easy removal and cleaning.

These and other objects will be apparent to those skilled in the art.

SUMMARY OF THE INVENTION

This invention comprises a hand splint having an elongated base member extending from the forearm of the patient to the palm of the patient's hand. A crossbar is secured to the body member adjacent the fingers of the patient, and the crossbar extends laterally or transversely with respect to the length of the base member.

A pad member is located on the inner surface of the body member and has a finger pad portion which extends around the crossbar to accommodate the curvature of the patient's fingers. The pad member and the finger pad member are detachably secured to the body member. Strap elements affix the splint to the forearm and wrist of the patient.

BRIEF DESCRIPTION OF THE DRAWINGS.

FIG. 1 is a bottom plan view of the hand splint of this invention mounted on a patient's forearm, wrist, and hand;

FIG. 2 is a view similar to that of FIG. 1 wherein the hand splint is removed from the patient's hand;

FIG. 3 is a side elevational view of the hand splint shown in FIG. 2;

FIG. 4 is an enlarged scale sectional view taken on line 4—4 of FIG. 3;

FIG. 5 is an enlarged scale sectional view taken on line 5—5 of FIG. 3;

FIG. 6 is a top plan view of the body member of the splint;

FIG. 7 is a bottom plan view of the body member of the hand splint opposite to the view shown in FIG. 6; and FIG. 8 is a bottom plan view of the pad means that is affixed to the surface of the body member shown in FIG. 6.

DESCRIPTION OF THE PREFERRED EMBODIMENT.

The numeral 10 designates the hand splint of this invention which includes an elongated base member 12 having a generally concave cross-sectional shape with an inside surface 12A and an outside surface 12B. The base member 12 is contoured at 14 to receive the heel and palm of a patient's hand. The base member 12 has an upper end 16 and a lower end 18. A crossbar 20 is also contoured and extends across the lower end 18 of the body member. The base member and the crossbar are preferably of integral construction and are normally made of a substantially rigid plastic material.

A pad member 22 (FIG. 8) has an upper end 24 and a lower end 26. The lower end 26 of pad member 22 terminates in a finger pad 28 of generally rectangular configuration. Tabs 30 are formed on the forward edge 32 of finger pad 28, and a rearward edge 34 therefor supports tab fasteners 36. The pad members 22 and 28 should be of soft pliable material and the outer surface thereof is adaptable for use with Velcro ®-type fasteners.

As shown in FIG. 6, the inner surface 12A of body member 12 has elongated Velcro ® fastener strips secured thereto in any convenient fashion to detachably receive the pad member 22. Straps 40 and 42 equipped with typical Velcro ® fasteners are secured to the outside surface 12B of base member 12 as best shown in FIG. 7.

The numeral 44 (FIG. 1) designates a patient's arm with forearm 46, wrist 48, palm 50, thumb 52, and fingers 54.

The normal use of this invention involves attaching the pad 22 (FIG. 8) to the inside surface 12A of base member 12 (FIG. 6) by means of the Velcro ® strip 38. The finger pad 28 is thereupon wrapped around the crossbar 20 and affixed in this position by the Velcro ® fasteners on tabs 30 and 36. The wrapped condition of finger pad 28 on crossbar 20 is best shown in FIGS. 2 and 3.

The assembled hand splint is then placed in position on the patient's arm as shown in FIG. 1, and the straps 40 and 42 are used to securely hold the splint to the patient's arm.

Contracture of a patient's fingers results in the finger and thumb being tightly withdrawn into a fist position. The splint of this invention should be utilized before this extreme fist position is reached. The fingers 54 of the patient are allowed to encircle the finger pad 28 as shown in FIG. 1. Various degrees of curvature of the patient's fingers can be accommodated by using a finger pad structure of different thicknesses. The soft pliable structure of pad 22 as well as the finger pad 28 is comfortable for the patient and does not in any way irritate the patient's arm or hands.

The pad 22 and finger pad 28 can be easily removed from the patient's hand and from the base member 12 for laundering purposes by merely reversing the steps outlined heretofore.

It is therefore seen that this invention will accomplish at least all of the stated objectives.

I claim:

1. A contour hand splint, comprising, an elongated base member having a length extending from an upper end to a lower end, with the upper end being normally positioned adjacent the forearm of a patient, and the lower end positioned adjacent to the palm of a patient's hand, said length supporting the patient's wrist between said upper and lower ends, means for securing said base member to the patient's arm, a cross member of integral construction with said base member on the lower end of said base member and being at right angles to the length thereof, a single pad member on said base member and being positioned between said base member and the forearm, wrist and palm of the patient, said pad member having a lower end forming a finger pad means wrapped around said crossbar so that the fingers of the patient can partially encircle said crossbar to resist contracture of the fingers, and releasable means on said finger pad means detachably maintaining said finger pad means in its wrapped position on said crossbar; said releasable means comprising tabs wrapped around said crossbar on opposite sides of said base member.

2. The hand splint of claim 1 wherein said finger pad means is generally rectangular in shape with forward and rearward edges, and said releasable means comprising tab fastener means on said edges to engage each other to maintain said finger pad means in its wrapped position on said crossbar.

3. The hand splint of claim 1 wherein said crossbar is concave in shape.

4. The invention of claim 1 wherein said cross member is of uniform cross section.

* * * * *